United States Patent [19]

Prescott

[11] Patent Number: 5,061,280
[45] Date of Patent: Oct. 29, 1991

[54] OSSICULAR PROSTHESIS

[75] Inventor: Anthony D. Prescott, Arlington, Tenn.

[73] Assignee: Microtek Medical, Inc., Columbus, Miss.

[21] Appl. No.: 418,211

[22] Filed: Oct. 6, 1989

Related U.S. Application Data

[63] Continuation-in-part of Ser. No. 332,742, Apr. 4, 1989, abandoned.

[51] Int. Cl.⁵ ............................................... A61F 2/18
[52] U.S. Cl. ....................................................... 623/10
[58] Field of Search ........................ 623/10, 11, 16, 66

[56] References Cited

U.S. PATENT DOCUMENTS 4,676,796 6/1987 Merwin et al. ....................... 623/10

OTHER PUBLICATIONS

Richards Medical Company, "SHEA Prosthesis & Wears Prosthesis & Richards Prosthesis" Microtek Medical Catalog, 1987.

Primary Examiner—David J. Isabella
Attorney, Agent, or Firm—Antonelli, Terry, Stout & Kraus

[57] ABSTRACT

An ossicular prosthesis including a head portion and a shaft portion, each formed of a biocompatible material, preferably a susceptible to human tissues adhesion, and an intermediate portion formed of a bendable biocompatible material. The intermediate portion includes a first end connected to the head portion, a second end connected to the shaft portion, and a bendable shank which permits adjustable of the angular orientation of the shaft portion with respect to the head portion, allowing the prosthesis to be implanted in a human ear with the head portion contacting the tympanic membrane or the malleus of the ear and with the shaft portion contacting the arch or limbs or the footplate of the stapes. The prosthesis head portion and shaft portion are preferably made of hydroxylapatite, to which human tissue adheres, aiding in securing the prosthesis in the middle ear.

70 Claims, 1 Drawing Sheet

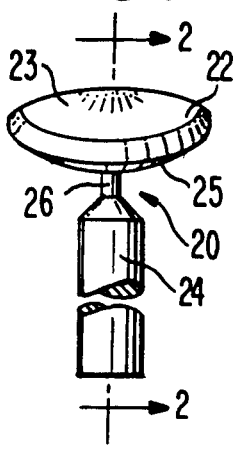
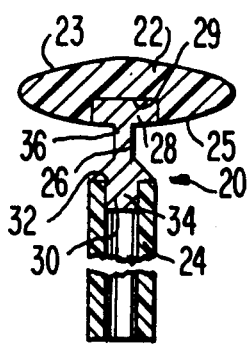
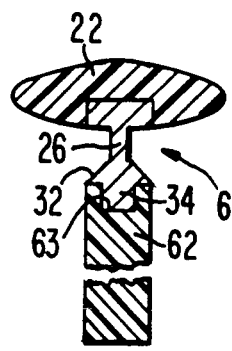
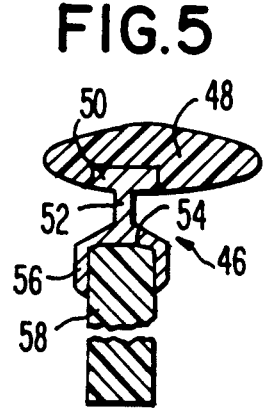
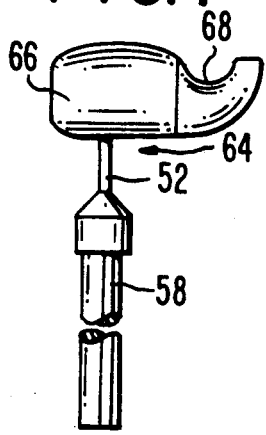
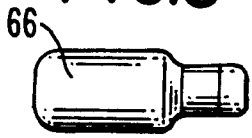
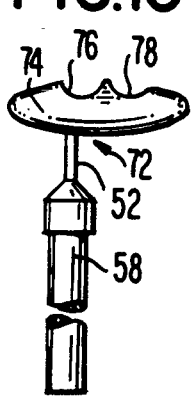
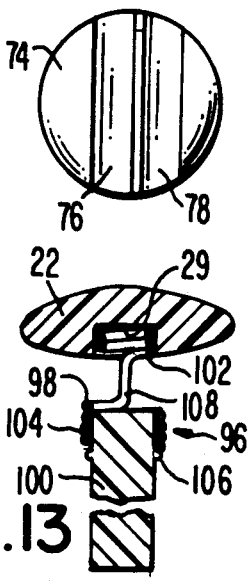
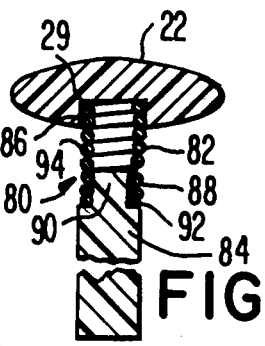
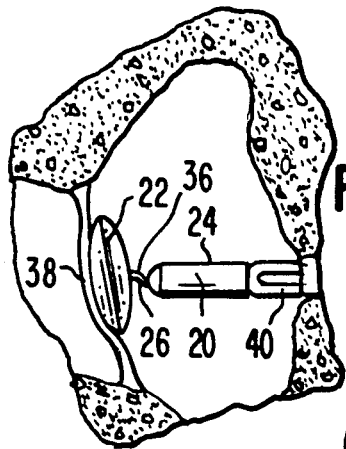
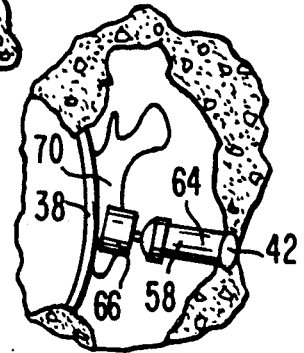
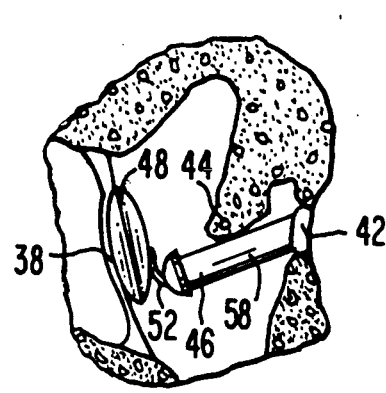

OSSICULAR PROSTHESIS

CROSS-REFERENCE TO RELATED APPLICATION

This application is a continuation-in-part of U.S. patent application Ser. No. 332,742 filed Apr. 4, 1989, now abandoned.

BACKGROUND OF THE INVENTION

The present invention pertains to improved ossicular prostheses. More particularly, the present invention pertains to bendable ossicular prostheses which can be shaped and sized to conform to the spacing in the middle ear of a person requiring such a prosthesis and which can be implanted in the middle ear without the necessity for an interfacing layer of human tissue.

The middle ear is an irregular, air filled space within which three auditory ossicles provide mechanical linkage between the tympanic membrane or ear drum and the opening to the inner ear, commonly referred to as the oval window. The three auditory ossicles are the malleus, the incus, and the stapes. The malleus includes a handle portion and a head portion. The handle portion contacts the tympanic membrane. The stapes includes an arch, having a pair of limbs, and a footplate. The footplate communicates with the oval window leading to the inner ear. The incus couples vibrations from the head portion of the malleus, caused by the malleus handle portion vibrating due to sound impinging on the tympanic membrane, to the arch of the stapes. The stapes footplate passes these sound vibrations to the inner ear. The lever action of the ossicles within the middle ear causes amplification of the sound vibrations, with the result that a greater vibrational force is experienced at the oval window than at the tympanic membrane.

Unfortunately, a number of middle ear conditions can result in damage to one or more of the ossicles, causing partial or total hearing loss. Various prostheses have been developed as replacements for the ossicles. One of the earliest such prostheses is a porous polyethylene strut. However, this device requires that a piece of cartilage, harvested from the patient at the time of the ear surgery, be positioned between the tympanic membrane and the head of the prosthesis. Treace, U.S. Pat. No. 4,510,627 shows an ossicular prosthesis having a porous body of a biocompatible material, such as polyethylene, surrounding an inner core of a biocompatible metallic material, such as stainless steel. The body has an enlarged head, which contacts a piece of human tissue that abuts the tympanic membrane, and a shaft, which contacts the stapes or the footplate of the stapes. The angle at which the shaft extends from the head can be varied, and the shaft itself can be bent to permit the device to adapt to various inner ear geometries. Nevertheless, the necessity for a human tissue interface between the head of the prosthesis and the tympanic membrane is a significant handicap in the use of such a prosthesis.

Another recently available ossicular prosthesis has a porous polyethylene head molded around a coiled wire, with the distal end of the wire extending from the head and inserted straight into a shaft of porous polyethylene or of Teflon. When this device is bent or adjusted, the wire can, unknown to the surgeon, migrate through the polyethylene shaft or head. As a result subsequent implantation in the middle ear could have hazardous results.

SUMMARY OF THE INVENTION

The present invention is an ossicular prosthesis including a head portion, an intermediate portion, and a shaft portion. The head portion has a surface configured for contacting either the tympanic membrane or the malleus, while avoiding sharp corners that might injure the tissue of the middle ear. The shaft portion is adapted to contact the footplate or the arch of the stapes. The head portion and the shaft portion are made of a biocompatible material, preferably, a hydroxylapatite material. Hydroxylapatite is a biocompatible material to which human tissue directly bonds. However, hydroxylapatite is a rigid brittle material which cannot be easily shaped or bent.

The intermediate portion of the present invention includes an enlarged first end which is secured to the prosthesis head portion, a bendable shank, and an enlarged second end which is secured to the prosthesis shaft portion. Accordingly, the ossicular prosthesis of the present invention can be bent to the required shape to permit it to be implanted in the middle ear of a patient regardless of the geometry of the middle ear. By "enlarged" ends is meant that the ends of the intermediate portion have a minimum diameter, or other cross-sectional dimension, that is substantially the same as or greater than the diameter of the shaft portion, with the result that the enlarged ends of the intermediate portion inhibit the intermediate portion from migrating through the head portion or the shaft portion. In one embodiment of the present invention, the bendable shank is made of a permanently bendable biocompatible material, such as stainless steel. By "permanently bendable" is meant a material which is non-resilient yet which can be readily bent by hand and which after bending retains its bent configuration until it is again bent, by hand or otherwise. As a result, when the ossicular prosthesis of this embodiment is bent to a specific configuration, by a doctor or other medical person during surgery to implant the prosthesis, the prosthesis retains that configuration.

In a second embodiment of the present invention, the intermediate portion is made of a wire member which is coiled at each end to form enlarged first and second ends, with a central segment connecting the two coiled ends. The central segment can be a coiled wire, coiled to the same or smaller diameter than the coiled ends, or it can be a straight wire, and it might even be a permanently bendable straight wire.

When the present invention is implanted in a middle ear having the stapes intact, the shaft portion can be an elongated tube-like member, fitting over the arch or limbs of the stapes. Where the stapes itself is damaged, the prosthesis shaft portion can be a solid rod-like member implanted to abut the footplate or a footplate prosthesis. Accordingly, implantation of the prosthesis is a less complex procedure.

One embodiment of the present invention replaces the malleus and the incus, and possibly the arch of the stapes, and so that embodiment is implanted in the middle ear with the head portion directly contacting the tympanic membrane and the shaft portion contacting either the arch or limbs or the footplate of the stapes. Another embodiment of the present invention replaces the incus, and possibly also the arch of the stapes, and so is implanted with the prosthesis head portion contacting the malleus head portion and with the prosthesis shaft portion contacting the arch or limbs or the footplate of the stapes.

In each embodiment of the present invention, the bendable intermediate portion, particularly the shank of the intermediate portion, can be bent to orient the prosthesis for the specific middle ear geometry. The enlarged ends of the intermediate portion permit the prosthesis to be implanted under compression between the tympanic membrane or malleus and the arch or limbs or the footplate of the stapes without danger of the intermediate portion migrating or pushing through the head portion or deeper into the shaft portion. Forming the head portion and the shaft portion of a biocompatible material to which human tissue directly bonds, such as a hydroxylapatite material, eliminates the need for human tissue to interface between the prosthesis and the tympanic membrane, the malleus, the arch or limbs, or the footplate.

BRIEF DESCRIPTION OF THE DRAWINGS

These and other aspects and advantages of the present invention are more apparent from the following detailed description and claims, particularly when considered in conjunction with the accompanying drawings in which like parts have like reference numerals. In the drawings:

FIG. 1 is a perspective view of a first embodiment of an ossicular prosthesis in accordance with the present invention, particularly suited for replacing the malleus and the incus of a middle ear;

FIG. 2 is a sectional view taken along line 2—2 of FIG. 1;

FIG. 3 is a schematic representation of a middle ear having implanted therein an ossicular prosthesis in accordance with FIG. 1, coupling the tympanic membrane and the arch of the stapes;

FIG. 4 is a sectional view of a second embodiment of an ossicular prosthesis in accordance with the present invention, particularly suited for replacing the malleus, the incus, and the arch of the stapes of a middle ear;

FIG. 5 is a sectional view of another embodiment of an ossicular prosthesis in accordance with the present invention, particularly suited for replacing the malleus, the incus and the arch of the stapes;

FIG. 6 is a schematic representation of a middle ear having implanted therein an ossicular prosthesis in accordance with FIG. 5, coupling the tympanic membrane and the footplate of the stapes;

FIG. 7 is a side elevational view of a further embodiment of an ossicular prosthesis in accordance with the present invention, particularly suited for replacing the incus and the arch of the stapes of a middle ear;

FIG. 8 is a top plan view of the prosthesis of FIG. 7;

FIG. 9 is a schematic representation of a middle ear having implanted therein an ossicular prosthesis in accordance with FIG. 7, coupling the malleus and the footplate;

FIG. 10 is a side elevational view of another embodiment of an ossicular prosthesis in accordance with the present invention, particularly suited for replacing the incus and the arch of the stapes of a middle ear;

FIG. 11 is a top plan view of the prosthesis of FIG. 10; and

FIGS. 12 and 13 are sectional views of further embodiments of an ossicular prosthesis in accordance with the present invention.

DETAILED DESCRIPTION OF PREFERRED EMBODIMENTS

FIGS. 1 and 2 depict an ossicular prosthesis 20 having a substantially circular head portion 22 and a tubular rod-like shaft portion 24, joined by an intermediate portion 26. Head portion 22 and shaft portion 24 are formed of a biocompatible material, preferably a hydroxylapatite material. Intermediate portion 26 is formed of a biocompatible, permanently bendable material such as stainless steel, platinum, titanium or tantalum.

As seen particularly in FIG. 2, head portion 22 has opposed convex upper and lower surfaces 23 and 25, respectively, which merge smoothly, thereby avoiding formation of sharp corners. Intermediate portion 26 includes an enlarged first end 28 which is secured within recess 29 in lower surface 25 of head portion 22, for example by being molded therein or by use of an adhesive such as a medical grade silicone adhesive or epoxy adhesive. Intermediate portion 26 further includes an enlarged second end 30 which is rigidly attached to shaft portion 24. Second end 30 of intermediate portion 26 includes a flange 32 and an insert segment 34. Insert segment 34 is sized to fit snugly within the interior of tubular shaft portion 24. Flange 32 has a maximum cross-sectional diameter substantially equal to the outside diameter of shaft portion 24, thus overlying substantially the complete proximal end of the tubular wall of shaft portion 24. Insert 34 can be retained in the end of tubular shaft portion 24 by a suitable medical grade silicone adhesive, by way of example. Alternatively, or additionally, first end 28 and insert segment 34 can be threaded into head portion 22 and shaft portion 24, respectively, or other suitable securing means could be used, as desired.

FIG. 3 illustrates ossicular prosthesis 20 implanted within the middle ear of a patient. Head portion 22 is attached to the typanic membrane or eardrum 38, while the distal end of tubular shaft portion 24 is positioned over the head of stapes 40. Shank 36 of intermediate portion 26 is permanently bent as required by the geometry of the specific middle ear to shape prosthesis 20 for implantation.

FIG. 4 illustrates a second embodiment of an ossicular prosthesis 60 in accordance with the present invention. Prosthesis 60 has a head portion 22 and an intermediate portion 26, of the same types as on prosthesis 20 of FIGS. 1 and 2, and a solid, rod-like shaft portion 62. The proximal end of solid shaft portion 62 has a recess 63 therein to receive insert segment 34 of intermediate portion 26. Flange 32 overlies substantially the complete proximal end of intermediate portion 62. Solid shaft portion 62 of prosthesis 60 makes prosthesis 60 suitable for implantation in a middle ear in which the arch of the stapes is deteriorated. In such instance, the stapes arch is removed, and the distal end of shaft portion 62 contacts the footplate of the middle ear.

FIG. 5 is a cross-sectional view of another embodiment of an ossicular prosthesis 46 in accordance with the present invention, having a head portion 48, an intermediate portion 52, and a solid, rod-like shaft portion 58. Head portion 48 is curved in the manner of head portion 22 in FIGS. 1-4. The enlarged first end 50 of intermediate portion 52 is affixed to head portion 48, as in the embodiment of FIGS. 1-4; however, first end 50 is offset from the center of head portion 48. The second end of intermediate portion 52 includes a flange 54 from which a sleeve 56 extends and encircles the proximal end of shaft portion 58. Thus, flange 54 overlies the complete proximal end of shaft portion 58.

The offset head portion 48 of prosthesis 46 permits use of prosthesis 46 in middle ear geometries where straight-line access to the central area of the tympanic membrane from the stapes is not available. FIG. 6 depicts a middle ear having an anomaly 44 blocking the straight line path between footplate 42 and the central region of tympanic membrane 38. As a consequence, ossicular prosthesis 46 has the distal end of its shaft portion 58 affixed to footplate 42, its intermediate portion 52 bent, and its offset head portion 48 contacting tympanic membrane 38, permitting implantation of prosthesis 46 around anomaly 44.

FIGS. 1-6 depict ossicular prostheses in accordance with the present invention for replacing the malleus, the incus, and the arch of stapes. FIGS. 7 and 8 depict an ossicular prosthesis 64 for replacing only the incus and the arch of the stapes. Prosthesis 64 includes a head portion 66, an intermediate portion 52, and a shaft portion 58. Intermediate portion 52 and shaft portion 58 are illustrated as being the same as intermediate portion 52 and shaft portion 58 of FIG. 5, although the configuration of FIGS. 1 and 2 or of FIG. 4, or a variation of any of these, would be similarly usable.

As seen from FIGS. 7 and 8, head portion 66 is a generally elongated, smoothly curved block having a convex top surface with a notch 68 therein for engaging the malleus handle, as illustrated in FIG. 9 which depicts prosthesis 64 implanted in a middle ear with the notch 68 of head portion 66 engaging the handle 70 of the malleus.

FIGS. 6 and 9 depict the distal end of shaft portion 58 affixed to footplate 42. Where the footplate has deteriorated, it can be removed and a vein graft implanted across the oval window, with the shaft portion affixed to the vein graft.

FIGS. 10 and 11 illustrate another embodiment of ossicular prosthesis 72 for replacing the incus and the arch of the stapes and including a smoothly curved head portion 74, an intermediate portion 52 and a shaft portion 58. Head portion 74 includes two notches 76 and 78, permitting selection of the notch to engage the handle of the malleus, in accordance with the middle ear geometry. By way of examples, notch 68 of FIGS. 7 and 8 and each notch 76 and 78 of FIGS. 10 and 11 can have a radius in the order of from about 0.5 mm to about 0.75 mm. Head portion 66 of FIGS. 7 and 8 can have a length, and head portion 74 of FIGS. 10 and 11 can have a diameter, in the order of about 3.0 to 4.0 mm. spacing between notches 76 and 78 permits selection of the appropriate notch for the particular geometry of the inner ear in which the prosthesis is to be installed. Notch 68 of prosthesis 64 in FIGS. 7 and 8 can be laterally displaced in the order of about 2.5 mm from the center line of shaft portion 58, while notches 76 and 78 of prosthesis 72 in FIGS. 9 and 10 can be laterally displaced in the order of about 1.5 mm and 3.5 mm, respectively, from the center line of shaft portion 58. Accordingly, a wide range of inner ear geometries can be accommodated.

FIG. 12 depicts an embodiment of an ossicular prosthesis 80 in accordance with the present invention including a head portion 22, an intermediate portion 82, and a shaft portion 84. Intermediate portion 82 has a first end 86 formed of a helically coiled wire segment which is secured within recess 29 in head portion 22. Intermediate portion 82 further has a second end 88 formed of a helically coiled wire segment. Coiled second end 88 encircles an insert segment 90 on the proximal end of shaft portion 84 and abuts shoulder 92. Shoulder 92 results from the extension of insert segment 90 from the balance of shaft portion 84 and so encircles shaft portion 84 adjacent the proximal end thereof. Shoulder 92 prevents second end 88 of intermediate portion 82 from moving further along shaft portion 84 than shoulder 92.

The central segment 94 of intermediate portion 82, joining first end 86 and second end 88, is a helically coiled wire which permits intermediate portion 82 to be bent as necessary to provide the desired configuration for the particular inner ear. If desired, first and second ends 86 and 88 can be more tightly coiled than central segment 94 as depicted in FIG. 12, with central segment 94, for example, being similar to the spring member found in some commercially available, inexpensive ball point pens. Coiled intermediate portion 82 functions as a shock absorber to prevent excess pressure or force from being transferred to incus 40 or footplate 42. The stiffness or springiness of coiled intermediate portion 82 may be controlled as desired and can provide a form of frequency tuning for prosthesis 80. In any event, intermediate portion 82 has sufficient stiffness to transmit sound vibrations sensed by the ear drum, yet has sufficient flexibility to absorb undesirable pressure changes such as might be experienced for example when driving in mountainous terrain, when in an elevator within a tall building, or when flying, particularly if the person utilizing prosthesis 80 has a cold or similar affliction.

FIG. 13 depicts a further embodiment of an ossicular prosthesis 96 in accordance with the present invention and including a head portion 22, an intermediate portion 98, and a shaft portion 100. First end 102 of intermediate portion 98 is formed as a helically coiled wire segment and is secured within recess 29 in head portion 22, while second end 104 of the intermediate portion is likewise formed of a helically coiled wire segment and encircles the proximal end of shaft portion 100, abutting shoulder 106 which encircles the main body of shaft portion 100 adjacent the proximal end thereof. Shoulder 106 thus prevents second end 104 of intermediate portion 98 from moving further along shaft portion 100 than shoulder 106.

The central segment 108 of intermediate portion 98 is a bendable wire shank joining first end 102 and second end 104 and permitting intermediate portion 98 to be bent as necessary to provide the desired configuration for the particular inner ear. If desired, central segment 108 can be formed of a permanently bendable material, as are the bendable shanks of intermediate portions 26 and 52 in FIGS. 1-10. Intermediate portions 82 and 98 might each be formed of a wire having a diameter in the order of about 0.004 to 0.012 inches and be stainless steel, platinum, titanium, tantalum, or other suitable biocompatible material.

In accordance with the present invention, any of the head portions 22, 48 or 66 can be incorporated into a prosthesis having either a tubular shaft portion 24 or a solid shaft portion 58, 62, 84 or 100, using an intermediate portion 26, 52, 82 or 98, as desired. The choice between these various combinations of embodiments may be based on the circumstances of the particular middle ear for which the particular prosthesis is to be used, as well as on manufacturing or other considerations. Preferably the head portion and the shaft portion of each prosthesis are made of a hydroxylapatite material. Pure dense hydroxylapatite is suitable. The shaft portion can be cut or ground to the desired length and angle for the specific middle ear geometry, using, for example, a diamond bur. Alternatively, a suitable material is a biocompatible composite made of an elastomeric material and bioactive ceramic or glass particles, for example a silicone or polyurethane material with hydroxylapatite particles such as disclosed in my co-pending U.S. patent application Ser. No. 07/310,646 filed Feb. 15, 1989. Such a material is easier to cut to the desired length and angle, while still adhering to human tissue.

In implanting a prosthesis in accordance with the present invention, the shaft portion can be cut to the required length and angle so that the tympanic membrane is slightly stretched when it is placed either over head portion 22 or 48, or when the malleus handle portion is engaged with prosthesis head portion 66 or 74, and when the shaft portion 24, 58, 62, 84, or 100 contacts the arch or limbs or the footplate of the stapes. The tissue of the tympanic membrane, the malleus, and the stapes adheres to the hydroxylapatite material, making unnecessary the use of a piece of human tissue, harvested from the patient during the prosthesis implantation, as an interface between the prosthesis and the tympanic membrane and/or stapes. A resorbable material, for example an absorbable gelatin sponge material such as that available under the trademark Gelfoam, can be utilized to hold the prosthesis in place until the tympanic membrane has healed, which generally occurs within a few days. The compression caused by the tympanic membrane then holds the prosthesis; however, care should be exercised to avoid sudden or sharp movement or bumps until sufficient tissue has adhered to the hydroxylapatite head portion and shaft portion to secure the prosthesis, which generally occurs within four or so weeks. Although the present invention has been described with reference to preferred embodiments, numerous rearrangements and alterations can be made, and still the result would be within the scope of the invention.

What is claimed:

1. An ossicular prosthesis comprising:
 a head portion formed of a rigid biocompatible material susceptible to human tissue adhesion;
 a shaft portion formed of a biocompatible material; and
 a bendable intermediate portion separate from said head portion and said shaft portion and having a first end connected to said head portion, a second end connected to said shaft portion, and a bendable shank coupling said first end and said second end, each of said intermediate portion first end and said intermediate portion second end having a cross-section larger than the cross-section of said shank, and said intermediate portion second end overlying substantially the complete proximal end of said shaft portion, said bendable shank permitting adjustment of the angular orientation of said shaft portion with respect to said head portion, allowing said prosthesis to be implanted in a human ear with said head portion directly contacting the tympanic membrane or the malleus of the ear and the shaft portion contacting the stapes or footplate of the ear, so that human tissue from the typanic membrane or malleus can adhere directly to said head portion, securing said prosthesis in the ear.

2. A prosthesis as claimed in claim 1 in which said head portion is substantially circular in cross-section.

3. A prosthesis as claimed in claim 1 in which said first end comprises a first helically coiled wire segment and said second end comprises a second helically coiled wire segment.

4. A prosthesis as claimed in claim 1 in which said intermediate portion comprises a helically coiled member.

5. A prosthesis as claimed in claim 1 wherein said head portion is formed of hydroxylapatite.

6. A prosthesis as claimed in claim 1 in which said intermediate portion second end includes a flange, substantially overlying said proximal end of said shaft portion, and an engaging portion fixedly engaging said shaft portion.

7. A prosthesis as claimed in claim 6 in which said engaging portion includes a sleeve segment extending from said flange portion and encircling said proximal end of said shaft portion.

8. A prosthesis as claimed in claim 6 in which said shaft portion includes a recess and said engaging portion includes an insert segment extending into said recess.

9. A prosthesis as claimed in claim 8 in which said shaft portion is a tubular shaft member.

10. A prosthesis as claimed in claim 8 in which said shaft portion is a solid rod having said recess formed in said proximal end thereof.

11. A prosthesis as claimed in claim 1 in which said head portion has a surface opposite said intermediate portion adapted for affixing to the tympanic membrane of a human ear.

12. A prosthesis as claimed in claim 11 in which said opposite surface is convex.

13. A prosthesis as claimed in claim 12 in which said headportion is substantially circular in cross-section.

14. A prosthesis as claimed in claim 1 in which said head portion has a surface opposite said intermediate portion adapted for affixing to the malleus of a human ear.

15. A prosthesis as claimed in claim 14 in which said opposite surface has a notch therein adapted for engaging the malleus.

16. A prosthesis as claimed in claim 15 in which the notch has a radius in the order of from about 0.5 mm to about 0.75 mm.

17. A prosthesis as claimed in claim 14 in which said opposite surface has two substantially parallel notches therein, each notch adapted for engaging the malleus, permitting selection of the notch utilized to engage the malleus.

18. A prosthesis as claimed in claim 17 in which the centerlines of the notches are spaced apart in the order of about 2.0 mm.

19. A prosthesis as claimed in claim 17 in which said head portion is substantially circular in cross-section.

20. A prosthesis as claimed in claim 17 in which each notch has a radius in the order of from about 0.5 mm to about 0.75 mm.

21. A prosthesis as claimed in claim 20 in which the centerlines of the notches are spaced apart in the order of about 2.0 mm.

22. A prosthesis as claimed in claim 1 in which said intermediate portion bendable shank is permanently bendable.

23. A prosthesis as claimed in claim 22 in which said intermediate portion first end comprises a first helically coiled wire portion positioned within a recess in said head portion, and said intermediate portion second end comprises a second helically coiled wire portion encircling the proximal end of said shaft portion.

24. A prosthesis as claimed in claim 23 in which said shaft portion includes a shoulder member encircling said shaft portion adjacent said proximal end and forming a retainer to prevent said second helically coiled wire portion from moving further along said shaft portion than said shoulder member.

25. A prosthesis as claimed in claim 22 in which said intermediate portion second end includes a flange, substantially overlying said proximal end of said shaft portion and an engaging portion fixedly engaging said shaft portion.

26. A prosthesis as claimed in claim 25 in which said engaging portion includes a sleeve segment extending from said flange portion and encircling said proximal end of said shaft portion.

27. A prosthesis as claimed in claim 25 in which said shaft portion includes a recess and said engaging portion includes an insert segment extending into said recess.

28. A prosthesis as claimed in claim 27 in which said shaft portion is a tubular shaft member.

29. A prosthesis as claimed in claim 27 in which said shaft portion is a solid rod having said recess formed in said proximal end thereof.

30. A prosthesis as claimed in claim 1 in which said shaft portion is formed of a material susceptible to human tissue adhesion so that human tissue from the stapes or footplate can adhere directly to said shaft portion.

31. A prosthesis as claimed in claim 1 in which said head portion and said shaft portion are formed of hydroxylapatite.

32. A prosthesis as claimed in claim 30 in which said shaft portion is formed of a rigid material.

33. An ossicular prosthesis comprising:
a head portion formed of a rigid biocompatible material susceptible to human tissue adhesion;
a shaft portion formed of a biocompatible material; and
a bendable intermediate portion separate from said head portion and said shaft portion and having a first end connected to said head portion, a second end connected to said shaft portion, and a bendable shank coupling said first end and said second end, said bendable shank permitting adjustment of the angular orientation of said shaft portion with respect to said head portion, allowing said prosthesis to be implanted in a human ear with said head portion directly contacting the tympanic membrane or the malleus of the ear and the shaft portion contacting the stapes or footplate of the ear, so that human tissue from the tympanic membrane or malleus can adhere directly to said head portion, securing said prosthesis in the ear,
said head portion having a convex surface, opposite said intermediate portion, adapted for affixing to the tympanic membrane of a human ear.

34. A prosthesis as claimed in claim 33 in which said head portion is formed of hydroxylapatite.

35. A prosthesis as claimed in claim 33 in which said head portion is substantially circular in cross-section.

36. A prosthesis as claimed in claim 33 in which said shaft portion is formed of a material susceptible to human tissue adhesion so that human tissue from the stapes or footplate can adhere directly to said shaft portion.

37. A prosthesis as claimed in claim 36 in which said shaft portion is formed of a rigid material.

38. A prosthesis as claimed in claim 37 in which said head portion and said shaft portion are formed of hydroxylapatite.

39. An ossicular prosthesis comprising:
a head portion formed of a rigid biocompatible material susceptible to human tissue adhesion, said head portion having a surface with two substantially parallel notches therein, each notch adapted for engaging and affixing to the malleus of a human ear, permitting selection of the notch utilized to engage the malleus, each notch having a radius in the order of from about 0.5 mm to about 0.75 mm;
a shaft portion formed of a biocompatible material; and
a bendable intermediate portion separate from said head portion and said shaft portion and having a first end connected to a surface of said head portion opposite said notches, a second end connected to said shaft portion, and a bendable shank coupling said first end and said second end, said bendable shank permitting adjustment of the angular orientation of said shaft portion with respect to said head portion, allowing said prosthesis to be implanted in a human ear with said head portion directly contacting the tympanic membrane or the malleus of the ear and the shaft portion contacting the stapes or footplate of the ear, so that human tissue from the tympanic membrane or malleus can adhere directly to said head portion, securing said prosthesis in the ear.

40. A prosthesis as claimed in claim 39 in which said head portion is substantially circular in cross-section.

41. A prosthesis as claimed in claim 39 in which said head portion is formed of hydroxylapatite.

42. A prosthesis as claimed in claim 41 in which the centerlines of the notches are spaced apart in the order of about 2.0 mm.

43. A prosthesis as claimed in claim 39 in which said shaft portion is formed of a material susceptible to human tissue adhesion so that human tissue from the stapes or footplate can adhere directly to said shaft portion.

44. A prosthesis as claimed in claim 43 in which said shaft portion is formed of a rigid material.

45. A prosthesis as claimed in claim 44 in which said head portion and said shaft portion are formed of hydroxylapatite.

46. An ossicular prosthesis comprising:
a head portion formed of a rigid biocompatible material susceptible to human tissue adhesion, said head portion having a surface with two substantially parallel notches therein, each notch adapted for engaging and affixing to the malleus of a human ear, permitting selection of the notch utilized to engage the malleus, the centerlines of the notches being spaced apart in the order of about 2.0 mm;
a shaft portion formed of a biocompatible material; and
a bendable intermediate portion separate from said head portion and said shaft portion and having a first end connected to a surface of said head portion opposite said notches, a second end connected to said shaft portion, and a bendable shank coupling said first end and said second end, said bendable shank permitting adjustment of the angular orientation of said shaft portion with respect to said head portion, allowing said prosthesis to be implanted in a human ear with said head portion directly contacting the tympanic membrane or the malleus of the ear and the shaft portion contacting the stapes or footplate of the ear, so that human tissue from the tympanic membrane or malleus can adhere directly to said head portion, securing said prosthesis in the ear.

47. A prosthesis as claimed in claim 46 in which said head portion is formed of hydroxylapatite.

48. A prosthesis as claimed in claim 46 in which said head portion is substantially circular in cross-section.

49. A prosthesis as claimed in claim 46 in which said shaft portion is formed of a material susceptible to human tissue adhesion so that human tissue from the stapes or footplate can adhere directly to said shaft portion.

50. A prosthesis as claimed in claim 49 in which said shaft portion is formed of a rigid material.

51. A prosthesis as claimed in claim 50 in which said head portion and said shaft portion are formed of hydroxylapatite.

52. An ossicular prosthesis comprising:
a head portion formed of a rigid biocompatible material susceptible to human tissue adhesion and having a recess therein;
a shaft portion formed of a biocompatible material; and
a bendable intermediate portion separate from said head portion and said shaft portion and having a first helically coiled wire end portion positioned within the recess of said head portion, a second helically coiled wire end portion encircling the proximal end of said shaft portion, and a permanently bendable shank coupling said first end and said second end, said bendable shank permitting adjustment of the angular orientation of said shaft portion with respect to said head portion, allowing said prosthesis to be implanted in a human ear with said head portion directly contacting the tympanic membrane or the malleus of the ear and the shaft portion contacting the stapes or footplate of the ear, so that human tissue from the tympanic membrane or malleus can adhere directly to said head portion, securing said prosthesis in the ear.

53. A prosthesis as claimed in claim 52 in which said shaft portion includes a shoulder member encircling said shaft portion adjacent said proximal end and forming a retainer to prevent said second helically coiled wire portion from moving further along said shaft portion than said shoulder member.

54. A prosthesis as claimed in claim 52 in which said head portion is substantially circular in cross-section.

55. A prosthesis as claimed in claim 52 in which said head portion has a surface opposite said intermediate portion adapted for affixing to the tympanic membrane of a human ear.

56. A prosthesis as claimed in claim 52 in which said head portion has a surface opposite said intermediate portion adapted for affixing to the malleus of a human ear.

57. A prosthesis as claimed in claim 52 in which said head portion is formed of hydroxylapatite.

58. A prosthesis as claimed in claim 52 in which said shaft portion is formed of a material susceptible to human tissue adhesion so that human tissue from the stapes or footplate can adhere directly to said shaft portion.

59. A prosthesis as claimed in claim 58 in which said shaft portion is formed of a rigid material.

60. A prosthesis as claimed in claim 59 in which said head portion and said shaft portion are formed of hydroxylapatite.

61. An ossicular prosthesis comprising:
a head portion formed of a rigid biocompatible material susceptible to human tissue adhesion;
a shaft portion formed of a biocompatible material; and
a helically coiled intermediate portion separate from said head portion and said shaft portion and having a first end connected to said head portion, a second end connected to said shaft portion, and a bendable shank coupling said first end and said second end, said bendable shank permitting adjustment of the angular orientation of said shaft portion with respect to said head portion, allowing said prosthesis to be implanted in a human ear with said head portion directly contacting the tympanic membrane or the malleus of the ear and the shaft portion contacting the stapes or footplate of the ear, so that human tissue from the tympanic membrane or malleus can adhere directly to said head portion, securing said prosthesis in the ear.

62. A prosthesis as claimed in claim 61 wherein said head portion is formed of hydroxylapatite.

63. A prosthesis as claimed in claim 4 in which said helically coiled member includes a first end positioned within a recess in said head portion, a second end encircling the proximal end of said shaft portion, and a central segment connecting said first end and said second end.

64. A prosthesis as claimed in claim 63 in which said shaft portion includes a shoulder member encircling said shaft portion adjacent said proximal end and forming a retainer to prevent said intermediate portion second end from moving further along said shaft portion than said shoulder member.

65. A prosthesis as claimed in claim 63 in which said intermediate portion comprises a single helically coiled member with each of said first end and said second end more tightly coiled than said central segment.

66. A prosthesis as claimed in claim 63 in which said first end comprises a first helically coiled wire segment, said second end comprises a second helically coiled wire segment, and said central segment comprises a bendable wire shank joining said first and second helically coiled wire segments.

67. A prosthesis as claimed in claim 66 in which said bendable wire shank is permanently bendable.

68. A prosthesis as claimed in claim 61 in which said shaft portion is formed of a material susceptible to human tissue adhesion so that human tissue from the stapes or footplate can adhere directly to said shaft portion.

69. A prosthesis as claimed in claim 68 in which said shaft portion is formed of a rigid material.

70. A prosthesis as claimed in claim 69 in which said head portion and said shaft portion are formed of hydroxylapatite.

* * * * *